(12) United States Patent
Steckel et al.

(10) Patent No.: US 9,849,008 B2
(45) Date of Patent: *Dec. 26, 2017

(54) BIOABSORBABLE IMPLANTS

(71) Applicant: Zorion Medical, Inc., Zionsville, IN (US)

(72) Inventors: Mark Steckel, Glasgow (GB); Ioannis O. Pandelidis, Sharon, MA (US)

(73) Assignee: Zorion Medical, Inc., Zionsville, IN (US)

( * ) Notice: Subject to any disclaimer, the term of this patent is extended or adjusted under 35 U.S.C. 154(b) by 90 days.

This patent is subject to a terminal disclaimer.

(21) Appl. No.: 14/527,937

(22) Filed: Oct. 30, 2014

(65) Prior Publication Data

US 2015/0057742 A1 Feb. 26, 2015

Related U.S. Application Data

(62) Division of application No. 13/165,247, filed on Jun. 21, 2011, now Pat. No. 8,888,841.

(Continued)

(51) Int. Cl.
*A61F 2/06* (2013.01)
*A61F 2/86* (2013.01)
(Continued)

(52) U.S. Cl.
CPC .............. *A61F 2/86* (2013.01); *A61L 27/047* (2013.01); *A61L 27/54* (2013.01); *A61L 27/58* (2013.01);
(Continued)

(58) Field of Classification Search
CPC ........ A61L 31/148; A61L 31/10; A61L 31/06; A61F 2/82; C08L 67/04
See application file for complete search history.

(56) References Cited

U.S. PATENT DOCUMENTS 5,370,683 A 12/1994 Fontaine
6,287,332 B1 9/2001 Bolz et al.
(Continued)

FOREIGN PATENT DOCUMENTS

CN 101214396 A 7/2008
CN 101249286 A 8/2008
(Continued)

OTHER PUBLICATIONS

Motoyasu, "Development of Bioabsorbable Pure Magnesium Stent Material," Scientific Research Fund-Subsidized Project Database, Research Performance Report of Fiscal Year 2006, published in 2007, Research Project No. 18650134 URL, http://kaken.nii.ac.jp/d/p/18650134/2006/3/ja.ja.html.

(Continued)

*Primary Examiner* — Thomas J Sweet
*Assistant Examiner* — Tiffany Shipmon
(74) *Attorney, Agent, or Firm* — Quarles & Brady LLP

(57) ABSTRACT

A bioabsorbable implant including an elongated metallic element having more than 50% by weight a metal and being substantially free of rare earth elements, the elongated metallic element defining at least a portion of the bioabsorbable implant and including a wire formed into a discrete bioabsorbable expandable metal ring; at least two biostable ring elements, each biostable ring element having a biostable and radio-opaque metallic alloy, the bioabsorbable expandable metal ring being disposed adjacent to at least one of the biostable ring elements; at least one flexible longitudinal connector including a bioabsorbable polymer, the connector being disposed between at least two adjacent rings; and a coating having at least one pharmaceutically active agent disposed over at least a portion of one ring.

20 Claims, 12 Drawing Sheets

Related U.S. Application Data

(60) Provisional application No. 61/458,705, filed on Dec. 1, 2010, provisional application No. 61/399,340, filed on Jul. 12, 2010, provisional application No. 61/398,030, filed on Jun. 21, 2010.

(51) Int. Cl.
| | |
|---|---|
| A61L 27/04 | (2006.01) |
| A61L 27/54 | (2006.01) |
| A61L 27/58 | (2006.01) |
| A61L 31/02 | (2006.01) |
| A61L 31/14 | (2006.01) |
| A61L 31/16 | (2006.01) |
| A61L 31/18 | (2006.01) |
| C22C 1/00 | (2006.01) |
| C22C 23/00 | (2006.01) |
| C22F 1/06 | (2006.01) |
| A61F 2/89 | (2013.01) |
| A61F 2/82 | (2013.01) |

(52) U.S. Cl.
CPC ........... *A61L 31/022* (2013.01); *A61L 31/148* (2013.01); *A61L 31/16* (2013.01); *A61L 31/18* (2013.01); *C22C 1/00* (2013.01); *C22C 23/00* (2013.01); *C22F 1/06* (2013.01); *A61F 2/89* (2013.01); *A61F 2002/828* (2013.01); *A61F 2210/0004* (2013.01); *A61F 2250/0067* (2013.01); *A61F 2250/0071* (2013.01); *A61F 2250/0098* (2013.01)

(56) References Cited

U.S. PATENT DOCUMENTS

| | | | |
|---|---|---|---|
| 6,585,755 | B2 | 7/2003 | Jackson et al. |
| 6,602,282 | B1 | 8/2003 | Yan |
| 6,629,994 | B2 | 10/2003 | Gomez et al. |
| 6,652,579 | B1 | 11/2003 | Cox et al. |
| 6,713,119 | B2 | 3/2004 | Hossainy et al. |
| 6,730,116 | B1 | 5/2004 | Wolinsky et al. |
| 6,776,793 | B2 | 8/2004 | Brown et al. |
| 7,004,968 | B2 | 2/2006 | Lootz et al. |
| 7,018,401 | B1 | 3/2006 | Hyodoh et al. |
| 7,070,607 | B2 | 7/2006 | Murayama et al. |
| 7,083,640 | B2 | 8/2006 | Lombardi et al. |
| 7,192,443 | B2 | 3/2007 | Solem et al. |
| 7,674,416 | B2 | 3/2010 | Hong et al. |
| 7,727,272 | B2 | 6/2010 | Schlun et al. |
| 7,736,687 | B2 | 6/2010 | Sims et al. |
| 7,806,916 | B2 | 10/2010 | Delaloye et al. |
| 7,809,447 | B2 | 10/2010 | Dreier et al. |
| 7,833,260 | B2 | 11/2010 | Cottone et al. |
| 7,862,606 | B2 | 1/2011 | Lootz et al. |
| 7,862,607 | B2 | 1/2011 | McDermott et al. |
| 7,913,371 | B2 | 3/2011 | Klocke et al. |
| 7,939,146 | B2 | 5/2011 | Borck et al. |
| 2002/0174922 | A1 | 11/2002 | Ishii et al. |
| 2003/0130718 | A1 | 7/2003 | Palmas et al. |
| 2004/0034409 | A1 | 2/2004 | Heublein et al. |
| 2004/0073297 | A1 | 4/2004 | Rohde et al. |
| 2004/0098108 | A1 | 5/2004 | Harder et al. |
| 2004/0172123 | A1 | 9/2004 | Lootz et al. |
| 2005/0027350 | A1 | 2/2005 | Momma et al. |
| 2005/0096722 | A1 | 5/2005 | Lootz et al. |
| 2005/0125051 | A1 | 6/2005 | Eidenschink et al. |
| 2005/0266041 | A1 | 12/2005 | Gerold et al. |
| 2005/0276718 | A1 | 12/2005 | Burgermeister et al. |
| 2006/0018954 | A1 | 1/2006 | Kuttler |
| 2006/0020289 | A1 | 1/2006 | Kuttler |
| 2006/0020315 | A1 | 1/2006 | Geistert et al. |
| 2006/0020317 | A1 | 1/2006 | Flach et al. |
| 2006/0052863 | A1 | 3/2006 | Harder et al. |
| 2006/0052864 | A1 | 3/2006 | Harder et al. |
| 2006/0064160 | A1 | 3/2006 | Gerold et al. |
| 2006/0149352 | A1 | 7/2006 | Schlun |
| 2006/0188486 | A1 | 8/2006 | Carpenter et al. |
| 2006/0212108 | A1 | 9/2006 | Tittelbach |
| 2007/0156231 | A1* | 7/2007 | Weber ............... A61F 2/82 623/1.38 |
| 2007/0189915 | A1 | 8/2007 | Shrivastava et al. |
| 2007/0233232 | A1 | 10/2007 | St. Germain et al. |
| 2007/0299512 | A1 | 12/2007 | Korzuschnik et al. |
| 2008/0031765 | A1 | 2/2008 | Gerold et al. |
| 2008/0033530 | A1 | 2/2008 | Zberg et al. |
| 2008/0033531 | A1 | 2/2008 | Barthel et al. |
| 2008/0033533 | A1 | 2/2008 | Borck et al. |
| 2008/0033535 | A1 | 2/2008 | Mueller et al. |
| 2008/0033536 | A1 | 2/2008 | Wittchow |
| 2008/0033537 | A1 | 2/2008 | Tittelbach |
| 2008/0033538 | A1 | 2/2008 | Borck et al. |
| 2008/0033539 | A1 | 2/2008 | Sternberg et al. |
| 2008/0033576 | A1 | 2/2008 | Gerold et al. |
| 2008/0050413 | A1 | 2/2008 | Horvers et al. |
| 2008/0051866 | A1 | 2/2008 | Chen et al. |
| 2008/0051872 | A1 | 2/2008 | Borck |
| 2008/0058923 | A1 | 3/2008 | Bertsch et al. |
| 2008/0097575 | A1 | 4/2008 | Cottone |
| 2008/0103594 | A1 | 5/2008 | Loffler et al. |
| 2008/0131479 | A1 | 6/2008 | Weber et al. |
| 2008/0188927 | A1 | 8/2008 | Rohde et al. |
| 2008/0215140 | A1 | 9/2008 | Borck et al. |
| 2008/0243230 | A1 | 10/2008 | Lootz et al. |
| 2008/0243242 | A1 | 10/2008 | Kappelt et al. |
| 2008/0249608 | A1 | 10/2008 | Dave |
| 2008/0269872 | A1 | 10/2008 | Lootz et al. |
| 2008/0281400 | A1 | 11/2008 | Philipp et al. |
| 2008/0312736 | A1 | 12/2008 | Mueller et al. |
| 2009/0017088 | A1 | 1/2009 | Klocke et al. |
| 2009/0018648 | A1 | 1/2009 | Wittchow |
| 2009/0024210 | A1 | 1/2009 | Klocke et al. |
| 2009/0024211 | A1 | 1/2009 | Wittchow |
| 2009/0030506 | A1 | 1/2009 | Klocke et al. |
| 2009/0030507 | A1 | 1/2009 | Klocke et al. |
| 2009/0048660 | A1 | 2/2009 | Adden |
| 2009/0069884 | A1 | 3/2009 | Mueller |
| 2009/0076596 | A1 | 3/2009 | Adden et al. |
| 2009/0081313 | A1* | 3/2009 | Aghion ............... A61L 27/047 424/641 |
| 2009/0110750 | A1 | 4/2009 | Greener |
| 2009/0148496 | A1 | 6/2009 | Schmitz et al. |
| 2009/0164002 | A1 | 6/2009 | Becher et al. |
| 2009/0171452 | A1* | 7/2009 | Yamamoto ............ A61L 31/022 623/1.38 |
| 2009/0192594 | A1 | 7/2009 | Borck |
| 2009/0192595 | A1 | 7/2009 | Naqura et al. |
| 2009/0192596 | A1 | 7/2009 | Adden |
| 2009/0198320 | A1 | 8/2009 | Mueller et al. |
| 2009/0204082 | A1 | 8/2009 | Wesselmann et al. |
| 2009/0208555 | A1 | 8/2009 | Kuttler et al. |
| 2009/0228091 | A1 | 9/2009 | Surber et al. |
| 2009/0270979 | A1 | 10/2009 | Adden |
| 2009/0274737 | A1 | 11/2009 | Borck |
| 2009/0292351 | A1 | 11/2009 | McClain et al. |
| 2009/0306725 | A1 | 12/2009 | Hiromoto et al. |
| 2010/0010640 | A1 | 1/2010 | Gerold et al. |
| 2010/0022894 | A1 | 1/2010 | Tittelbach et al. |
| 2010/0023112 | A1 | 1/2010 | Borck et al. |
| 2010/0034899 | A1 | 2/2010 | Harder et al. |
| 2010/0049300 | A1 | 2/2010 | Harder |
| 2010/0076539 | A1 | 3/2010 | Klocke et al. |
| 2010/0076542 | A1 | 3/2010 | Orlowski |
| 2010/0076556 | A1 | 3/2010 | Tomantschqer et al. |
| 2010/0082092 | A1 | 4/2010 | Gerold |
| 2010/0087914 | A1 | 4/2010 | Bayer et al. |
| 2010/0087915 | A1 | 4/2010 | Bayer et al. |
| 2010/0087916 | A1 | 4/2010 | Bayer et al. |
| 2010/0106243 | A1 | 4/2010 | Wittchow |
| 2010/0119576 | A1 | 5/2010 | Harder et al. |
| 2010/0119581 | A1 | 5/2010 | Gratz et al. |
| 2010/0121432 | A1 | 5/2010 | Klocke et al. |
| 2010/0131052 | A1 | 5/2010 | Kappelt et al. |
| 2010/0137971 | A1 | 6/2010 | Lootz et al. |

(56) References Cited

U.S. PATENT DOCUMENTS

| | | |
|---|---|---|
| 2010/0137975 A1 | 6/2010 | Wittchow |
| 2010/0161030 A1 | 6/2010 | Bayer et al. |
| 2010/0161053 A1 | 6/2010 | Bayer |
| 2010/0171492 A1 | 7/2010 | Klocke et al. |
| 2010/0249900 A1 | 9/2010 | Sager et al. |
| 2010/0249904 A1* | 9/2010 | Takayuki ............ A61M 29/00 623/1.16 |
| 2010/0262221 A1 | 10/2010 | Schafer et al. |
| 2010/0262229 A1 | 10/2010 | Rohde |
| 2010/0272882 A1* | 10/2010 | Radhakrishnan ....... C23C 14/22 427/2.25 |
| 2010/0292639 A1 | 11/2010 | Schwitzer et al. |
| 2010/0312324 A1 | 12/2010 | Adden et al. |
| 2010/0324654 A1 | 12/2010 | Bayer et al. |
| 2010/0324659 A1 | 12/2010 | Mews et al. |
| 2011/0009952 A1 | 1/2011 | Bayer et al. |
| 2011/0029064 A1 | 2/2011 | Burpee et al. |
| 2011/0034991 A1 | 2/2011 | Barthel et al. |
| 2011/0076319 A1 | 3/2011 | Orlowski et al. |
| 2011/0077732 A1 | 3/2011 | Bayer et al. |
| 2011/0093061 A1 | 4/2011 | Lootz et al. |
| 2011/0112628 A1 | 5/2011 | Bayer |
| 2011/0130823 A1 | 6/2011 | Gerold et al. |
| 2011/0137395 A1 | 6/2011 | Farqahi |

FOREIGN PATENT DOCUMENTS

| | | |
|---|---|---|
| CN | 101385875 A | 3/2009 |
| CN | 101632842 A | 1/2010 |
| CN | 101721266 A | 6/2010 |
| DE | 102007030438 A | 1/2009 |
| EP | 1270023 A2 | 1/2003 |
| EP | 1795215 A2 | 6/2007 |
| EP | 1835043 A1 | 9/2007 |
| EP | 1959025 A1 | 8/2008 |
| EP | 2169090 A1 | 3/2010 |
| EP | 2189169 A1 | 5/2010 |
| JP | 60-174156 | 11/1985 |
| JP | 2001-96395 | 4/2001 |
| JP | 2005-253959 | 9/2005 |
| JP | 2009-178293 | 8/2009 |
| WO | 2005/102222 A2 | 11/2005 |
| WO | 2007/058276 A1 | 5/2007 |
| WO | 2007/136969 A2 | 11/2007 |
| WO | 2008/106271 A2 | 9/2008 |
| WO | 2008/118606 A2 | 10/2008 |
| WO | 2010/017959 A2 | 2/2010 |
| WO | 2010/132910 A1 | 11/2010 |

OTHER PUBLICATIONS

Tajima, et al., "Tensile deformation of single crystal pure magnesium rods produced by the OCC process," Summary of Presentations at the 112th Spring Conference of Japan Institute of Light Metals, Apr. 11, 2007, pp. 357-358.

Fan, et al., Continuous casting technology of single crystal metals, Chinese Journal of Materials Research, (Jun. 1996), vol. 10, No. 3, pp. 264-266.

International Search Report and Written Opinion, Application No. PCT/US2011/062922, dated Oct. 26, 2012, 18 pages.

International Search Report and Written Opinion, Application No. PCT/US2011/041258, dated Jan. 31, 2012, 17 pages.

Invitation to Pay Additional Fees with Partial International Search for International Application No. PCT/US2011/041258, dated Oct. 10, 2011, 5 pages.

Japanese Patent Office—English translated office action for Japanese Application No. 2013-516690, dated May 28, 2014.

Kim, et al., An Experimental Study on Process Variables in Crystal Growth by Ohno Continuous Casting, Metallurqical Transactions A, vol. 19A, Jul. 1988—pp. 1849.

Kim, et al., Operating parameters for the continuous unidirectional solidification of the Al-1 wt.% Si Alloy drawn to fine wire, Metals and Materials, vol. 6, No. 6 (2000), pp. 491-495.

Ohno, Casting of Near Net Shape Products, The Metallurgical Society, Edited by Y. Bahai, p. 177, 1988.

Ohno, Magnesium Ingot by Ohno Continuous Casting Process, Light Metal Age, Fellom, San Francisco, CA, US, vol. 16, No. 5/06, Jun. 1, 1988, p. 6/07.

Partial International Search Report and Invitation to Pay Additional Fees, Application No. PCT/US2011/062922, dated Jul. 2, 2012, 9 pages.

Zhang, et al., Microstructure of binary Mg—Al eutectic alloy wires produced by the Ohno continuous casting process, Acta Metallurgica Sinica (English Letters) vol. 21, No. 4 pp. 275-281 Aug. 2008.

* cited by examiner

BIOABSORBABLE IMPLANTS

CROSS-REFERENCE TO RELATED APPLICATIONS

This application is a divisional of U.S. patent application Ser. No. 13/165,247, filed Jun. 21, 2011, and entitled "Bioabsorbable Implants," the disclosure of which in turn claims priority to, and the benefit of, U.S. Provisional Patent Application Ser. No. 61/398,030 filed Jun. 21, 2010, U.S. Provisional Patent Application Ser. No. 61/399,340 filed Jul. 12, 2010, and U.S. Provisional Patent Application Ser. No. 61/458,705, filed Dec. 1, 2010. The disclosures of all four of these applications are incorporated by reference herein in their entireties.

TECHNICAL FIELD

This application relates generally to implants, and more specifically to bioabsorbable intraluminal implants.

BACKGROUND OF THE INVENTION

The field of coronary angioplasty and stenting has made dramatic progress in treatment of coronary heart disease through at least three generations of product technology. However, each generational advancement has been accompanied by a new challenge or failure mode of the therapy. Balloon angioplasty therapy improved acute luminal flow, but vessel recoil and remodeling resulted in high restenosis rates. Bare metal stenting lowered restenosis rates and minimized abrupt closure events, but restenosis rates were still high due to stent mechanical injury and resulting smooth muscle cell (SMC) migration and proliferation into the lumen. Drug eluting stents cut the retreatment rate again significantly by addressing the SMC proliferation with a pharmaceutical agent, but again was accompanied by a "new" complication, late stent thrombosis (LST) and the accompanying extended use of anti-coagulants. LST is associated with high mortality rates, although the frequency of the events is relatively low. The apparent factors driving this serious complication appear to be the loss of vaso-motion and delayed healing of a functional endothelium.

Attempts to use magnesium and its alloys as a temporary implant biomaterial, including in cardiovascular stents, have been hindered by poor control over the rate and uniformity of the metal's degradation (metallic corrosion rate), fragmentation and absorption processes in local tissue. Previous attempts to control degradation or corrosion rates have focused on alloying with rare earth and other heavy metal elements of unknown biocompatibility, yielding slower metallic corrosion rates but unproven benefits in clinical performance. Although these approaches have merit for non-medical applications such as commercial or aerospace castings, they are sub-optimal for an absorbable implant grade material that will eventually be fully metabolized by the host tissue, releasing alloying elements of unknown biocompatibility. Furthermore, conventional approaches to corrosion control of magnesium alloys have focused solely on preventing the initial mechanical failure of the given article by retarding the degradation process either by a surface passivation layer, or changing the local corrosion potential of the alloy. No consideration has been given to controlling the process of fragmentation, disintegration and absorption following the initial mechanical failure. For many implant applications, the timing and nature of the full degradation process, starting with the as-implanted metal article to the final clearance of the alloy mass and its degradants from the anatomical site, is critical regarding the performance of the medical device.

For absorbable metal implants, the corrosion process and ultimate mechanical properties are strongly dominated by the polycrystalline grain structure of the metal. Corrosion can proceed along grain boundaries due to localized galvanic reactions between Mg and more noble metals that are excluded from the crystal lattice during solidification from the melt. Cavitation and cracking can start at the grain boundaries due to the cyclic fatigue from pulsatile loading in the artery, resulting in gross mechanical failure of the implant long before a significant volume fraction of Mg has experienced corrosion. This can significantly shorten the implant's functional life, i.e., the period of time where the implant is mechanically intact and load bearing, and extend the time when large metallic fragments can cause injury and inflammation at the implant site.

One such implant application is absorbable metal stents for vascular or luminal scaffolding, such as stents for treatment of coronary artery disease. In this application, the stents provide temporary scaffolding through the healing process related to the local injury caused by the high pressure angioplasty balloon used to open the stenosed or partially blocked artery. The metal scaffold is typically required only for a period of days to weeks to prevent abrupt closure of the vessel from spasm, minimize elastic recoil, and as a substrate to deliver a controlled release drug-polymer formulation to the site of injury. After this period, any remnant of the alloy or its degradants may be a liability, since it can act as a foreign body prolonging an inflammatory response and delaying healing. Furthermore, if the stent remnants remain present in the lumen in solid form through the period of extracellular matrix deposition and scar formation, then the stent remnants themselves become a source of lumen obstruction and participate in a new form of restenosis unknown to conventional permanent stents.

An alternative design approach towards absorbable stents utilizes highly crystalline absorbable polymers such as PLLA for the structural elements of the stent scaffold. This approach has a more controlled degradation process, but suffers from low radial stiffness that is needed to open the artery, i.e., so called acute gain, and limited ductility making stent-artery sizing problematic.

The current standard of care for treating most de novo coronary lesions is the implantation of a permanent implant known as a drug eluting stent or DES. The DES is a third generation angioplasty device for treating coronary stenosis, with significantly lower re-intervention rates than either bare metal stents or balloon angioplasty. This generation technology is a permanent implant, typically comprising a high strength and high radiopacity metal such as cobalt chrome or platinum enriched stainless steel, coated with a formulation of an anti-proliferative drug in a controlled release polymer.

The next generation of technology is a fully absorbable DES, i.e. the entire mechanical scaffolding (stent) and the drug formulation is broken down in the body and absorbed. The working hypothesis is that any permanent foreign body at the site can prolong inflammation and delay healing and restoration to its native state. The major complication associated with drug eluting stents is late stent thrombosis, which is believed to result from this delayed healing.

The primary focus of fully absorbable stents has been on achieving the necessary hoop strength and stiffness to bear the high mechanical stresses in the coronary arteries, but a second key characteristic that is required is radio-opacity to enable the physician to visualize the stent after implantation.

Since the two primary materials used in experimental absorbable stents, L-poly lactic acid (pLLA) and magnesium alloys, are both essentially radio-transparent, small disc-shaped radio-markers comprised of platinum, platinum-iridium, or tantalum are typically integrated into the end of the laser cut stent body. If there are 2 or 3 radio-markers on each end of the stent, then the location and level of deployment can be visualized by angiography during a procedure, even if the bulk of the stent is not radio-opaque. This is a well-established approach for nickel-titanium permanent stents which possessed low intrinsic radio-opacity.

The problems with this conventional approach for metallic absorbable stents, such as magnesium-based alloys, are that fragmentation occurs within weeks, and the relatively large radio-markers (approximately 1.0 mm diameter by 125 micron thick) may migrate from the implantation site and become emboli, potentially resulting in a serious infarction of distal coronary vessels. Ideally, the radio-marker for an absorbable magnesium stent would be self-sufficient regarding prevention of migration, and its safety not be compromised through magnesium fragmentation process.

SUMMARY OF THE INVENTION

According to one aspect of the present teachings, a bioabsorbable implant including an elongated metallic element is provided, the metallic element having more than 50% by weight a metal and being substantially free of rare earth elements. According to one illustrative embodiment, the elongated metallic element defines at least a portion of the bioabsorbable implant and includes a wire formed into a discrete bioabsorbable expandable metal ring. The bioabsorbable implant further comprises at least two biostable ring elements, wherein each biostable ring element has a biostable and radio-opaque metallic alloy, and the bioabsorbable expandable metal ring is disposed adjacent to at least one of the biostable ring elements. The bioabsorbable implant also includes at least one flexible longitudinal connector having a bioabsorbable polymer, the connector being disposed between at least two adjacent rings, and a coating having at least one pharmaceutically active agent disposed over at least a portion of one ring.

According to yet another aspect of the present teachings, a bioabsorbable implant including a directionally solidified and elongated metallic element is provided, the metallic element having <0.1 weight percent of rare earth metals and more than 80% by weight a metal selected from the group consisting of magnesium, iron, zinc, manganese and combinations thereof. The elongated metallic element defines at least a portion of the bioabsorbable implant and comprises a wire formed into a discrete bioabsorbable expandable metal ring. The bioabsorbable implant further comprises at least two biostable ring elements, wherein each biostable ring comprises a biostable and radio-opaque metallic alloy, and wherein the bioabsorbable expandable metal ring is disposed adjacent to at least one of the biostable rings. In accordance with certain aspects herein, at least one flexible longitudinal connector comprises a bioabsorbable polymer that is disposed between at least two adjacent rings, and the implant further comprises a coating having at least one pharmaceutically active agent disposed over at least a portion of one ring. According to certain illustrative aspects of the present teachings, the wire defines at least one of a continuous single grain and a columnar microstructure including one or more columnar grains extending substantially the entire length of the implant, and the wire exhibits enhanced strength and physical integrity post-implantation by being substantially free of grain boundaries containing impurities.

The use of magnesium and its alloys, as well as alloys of iron, zinc, calcium, and manganese, as an absorbable biomaterial for temporary implants has been hindered by poor control over the rate and uniformity of the metals strength and mass loss. A novel approach described herein improves these properties through processing by directional solidification and the formation of single crystal or poly-columnar crystal micro-structures. The resulting structure degrades primarily by surface erosion, whereas conventional polycrystalline metal breaks rapidly along grain boundaries resulting in early mechanical failure, followed by slow full absorption.

In particular, embodiments of the invention address the deficiencies of conventional polycrystalline metal-based alloys of magnesium, iron, zinc, calcium, and manganese for elongated implants through control of the microstructure to yield either single crystal or columnar crystal structures that extend continuously for the length of the implant or implant sub-component. This structure yields a more controlled and uniform strength retention and degradation profile than conventional polycrystalline structures, which rapidly lose strength due to corrosion along grain boundaries but then have long absorption times due to the slow corrosion rate of the bulk of the alloy within the individual grains. In some embodiments, the implants of this invention lose strength and mass in parallel as the cross-sectional area is reduced through surface erosion.

Moreover, a fourth generation of cardiovascular implants are described; these implants are based on bioabsorbable stent scaffolds that may resolve both the vaso-motion and foreign body issues, by fully absorbing in a period of 3-24 months post-implantation.

Embodiments of the invention address the deficiencies of previous absorbable intra-luminal implants for local drug delivery by a composite design that utilizes absorbable metal and absorbable polymer technologies. The design includes a plurality of discrete rings or a continuous helix of ring-like structures formed of an absorbable metal, such as magnesium, zinc, or iron and their respective alloys, to achieve high radial force and stiffness necessary to prevent vessel recoil. Unlike current metal stents, the structural rings are not interconnected by metal elements, but instead by flexible absorbable polymer connectors with a different absorption time than the metal ring elements. Finally, the device serves as a drug delivery substrate by inclusion of an active pharmaceutical, preferably an anti-proliferative agent to smooth muscle cells that is eluted at a controlled rate over a period of weeks to months.

Embodiments of the invention include a hybrid intraluminal implant that consists of a plurality of cylindrical or "ring" segments, with alternating segments of bioabsorbable and biostable (permanent, non-degrading) materials. The "end" segments (proximal and distal) include a biostable and radio-opaque material such as a cobalt chrome alloy or stainless steel, and at least one inner ring segment comprising or consisting essentially of bioabsorbable material such as magnesium or its alloys. The ring segments are connected by polymeric connectors to avoid uncontrolled galvanic reactions between the permanent and absorbable metals in the presence of physiological fluid containing chlorides (saline). The implant's utility is enhanced by incorporation of an anti-proliferative drug with sustained release.

The acute performance of the hybrid stent is similar to conventional DES implants regarding acute luminal gain.

The bioabsorbable segments are fully absorbed in 6 months allowing endothelial healing and return of vaso-motion. The biostable ring segments are permanent radiomarkers that are self-sufficient for preventing migration and embolization. The biostable segments also provide load sharing to the adjacent absorbable metal segments through the polymer connectors, reducing lumen loss during the absorbable segment fragmentation period.

In an aspect, embodiments of the invention include a bioabsorbable implant including an elongated metallic element having more than about 50% by weight the metal magnesium, iron, zinc, calcium, or manganese, and/or combinations or alloys thereof and being substantially free of rare earth metals, namely the 15 lanthanoid elements, i.e., the elements having a proton number of 57-71, scandium, and yttrium. The elongated metallic element may define at least a portion of the bioabsorbable implant.

One or more of the following features may be included. The metal may define a continuous single grain and/or a columnar microstructure. The metal may define a columnar microstructure including grains having an average grain length of at least about 1 mm, and an average grain diameter of less than about 0.2 mm. The average grain length may be at least about 10 mm and/or the average grain diameter may be less than about 3 mm. The continuous single grain may have an aspect ratio of grain length to grain diameter of at least 10:1. The columnar microstructure may include grains having an aspect ratio of grain length to grain diameter of at least 10:1.

The elongated metallic element may be a wire, rod, and/or a hollow tube. The wire may have a diameter of less than about 0.2 mm.

The bioabsorbable implant may be an intraluminal device, a ligating clip, a ligating clip component, a bone fixation device (e.g., a plate, a pin, or a screw), or a bone-to-soft-tissue fixation device (e.g., a suture anchor, an interference screw, and a cross pin).

The description of elements of the embodiments of other aspects of the invention may be applied to this aspect of the invention as well.

In another aspect, embodiments of the invention include a bioabsorbable implant including an elongated metallic element having more than about 50% by weight a metal and being substantially free of rare earth elements, the elongated metallic element defining at least a portion of the bioabsorbable implant and including a wire formed into a bioabsorbable continuous helical sinusoid.

One or more of the following features may be included. The metal may be magnesium, iron, zinc, calcium, or manganese and/or combinations or alloys thereof. The wire may define at least one of a continuous single grain and a columnar microstructure.

The description of elements of the embodiments of other aspects of the invention may be applied to this aspect of the invention as well.

In yet another aspect, embodiments of the invention include a bioabsorbable implant including an elongated metallic element having more than about 50% by weight a metal and being substantially free of rare earth elements. The elongated metallic element may define at least a portion of the bioabsorbable implant and may include a wire formed into a first bioabsorbable expandable metal ring and a second bioabsorbable expandable metal ring. The bioabsorbable implant may also include at least one flexible longitudinal connector including an absorbable polymer and connecting the first and second expandable metal rings. A coating including a pharmaceutically active agent may be disposed over at least a portion of at least one of the first and second metal rings and the longitudinal connector.

One or more of the following features may be included. The metal may be magnesium, iron, zinc, calcium, or manganese, and/or combinations or alloys thereof. At least one of the expandable metal rings comprises a wire and may define a single grain and/or a columnar microstructure. At least one of the expandable metal rings may include a stud configured for coupling with an adjacent feature.

The at least one flexible longitudinal connector may include a biodegradable homopolymer and/or a aliphatic polyester such as lactic acid, lactide, glycolic acid, glycolide, caprolactone, dioxanone, trimethylcarbonate, and co-polymers and blends thereof.

The at least one flexible longitudinal connector may include directionally oriented absorbable filaments extending along a length of the bioabsorbable implant and/or extruded tubes of absorbable polymer. At least one of the expandable rings may form an aperture adapted for coupling with the at least one flexible longitudinal connector.

The pharmaceutically active agent may include or consist essentially of, e.g., a potent anti-proliferative to human smooth muscle cells, taxane, an mTOR agent, and/or a chemoactive agent suitable for cancer treatment.

The description of elements of the embodiments of other aspects of the invention may be applied to this aspect of the invention as well.

In another aspect, embodiments of the invention may include a bioabsorbable implant including an elongated metallic element having more than about 50% by weight a metal and being substantially free of rare earth elements. The elongated metallic element may define at least a portion of the bioabsorbable implant, and may include a wire formed into a discrete bioabsorbable expandable metal ring. The bioabsorbable implant may also include at least two biostable ring elements, each biostable ring including a biostable and radio-opaque metallic alloy, with the bioabsorbable expandable metal ring being disposed adjacent at least one of the biostable rings. At least one flexible longitudinal connector including a bioabsorbable polymer may be disposed between at least two adjacent rings. A coating including at least one pharmaceutically active agent may be disposed over at least a portion of one ring.

One or more of the following features may be included. The metal may be magnesium, iron, zinc, calcium, or manganese, and/or combinations or alloys thereof. At least two of the biostable rings may include a laser-machined hypo-tube made of, e.g., cobalt, chrome, stainless steel, titanium, or iron and/or alloys thereof.

At least one of the discrete biostable rings may define an aperture and/or a stud configured to couple with the at least one flexible longitudinal connector.

The at least one flexible longitudinal connector may include a biodegradable homopolymer and/or an aliphatic polyester, e.g., lactic acid, lactide, glycolic acid, glycolide, caprolactone, dioxanone, trimethylcarbonate, and co-polymers and blends thereof. The at least one flexible longitudinal connector may include directionally oriented absorbable filaments extending along a length of the bioabsorbable implant and/or extruded tubes of absorbable polymer.

The pharmaceutically active agent may include or consist essentially of a potent anti-proliferative to human smooth muscle cells, taxane, an mTOR agent, and/or a chemoactive agent suitable for cancer treatment.

The description of elements of the embodiments of other aspects of the invention may be applied to this aspect of the invention as well.

BRIEF DESCRIPTION OF THE DRAWINGS

The following drawings are not necessarily to scale, emphasis instead being placed generally upon illustrating the principles of the invention. Moreover, the above-mentioned aspects of the present invention and the manner of obtaining them will become more apparent and the invention itself will be better understood by reference to the following description of the embodiments of the invention taken in conjunction with the accompanying drawings, wherein.

Figure 1:
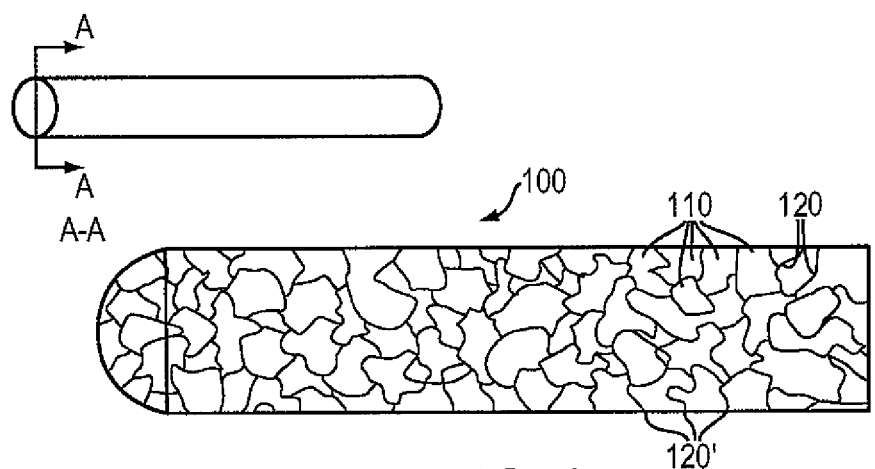
FIG. 1 is a schematic diagram of a segment of an elongated implant or sub-component such as a wire or pin with a conventional polycrystalline grain structure.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the disclosed aspects of the invention, as generally described herein, and illustrated in the Figures, may be arranged, substituted, combined, and designed in a wide variety of different configurations, all of which are explicitly contemplated and should be construed as being incorporated into this disclosure.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the specific methods and materials are now described. Moreover, the techniques employed or contemplated herein are standard methodologies well known to one of ordinary skill in the art and the materials, methods and examples are illustrative only and not intended to be limiting.

Referring to FIG. 1, a segment of an elongated implant 100 or sub-component such as a wire or pin with a conventional polycrystalline grain structure in cross-section A-A, has a plurality of grains 110 separated by grain boundaries 120. Grain boundaries 120' that are aligned perpendicularly to the primary loading axis may be initiation points for premature failure due to accelerated corrosion or crack formation from fatigue.

Figure 2:
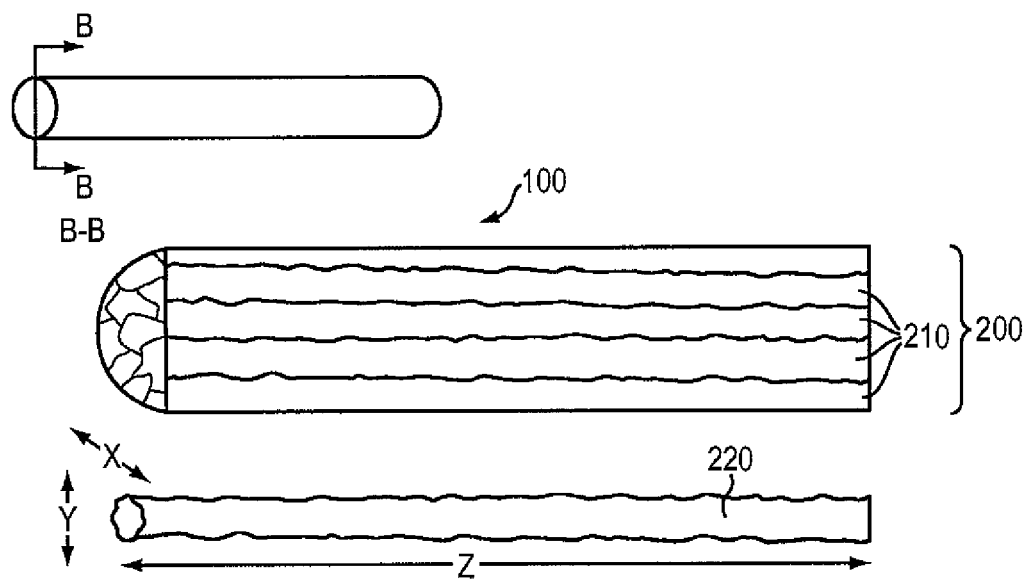
FIG. 2 is a schematic diagram of a segment of an elongated implant or sub-component processed by directional solidification that yields a plurality of columnar crystals in accordance with an embodiment of the invention.

In contrast, the crystal structure in accordance with embodiments of the invention may be either single crystal (i.e., a continuous single grain) or columnar crystal structures (i.e., a columnar microstructure) that extend continuously for the length of the implant or implant sub-component. Referring to FIG. 2, a bioabsorbable implant may include an elongated metallic element or sub-component that may be formed by directional solidification that yields a columnar microstructure 200 plurality of columnar crystals 210 that extend essentially the full functional length of the implant 100. A single crystal structure 220 that is essentially without grain boundaries is shown for clarity, with dimensions of z>>x, z>>y.

If the metal defines a columnar microstructure 200, the columnar microstructure may include grains having an average grain length of preferably at least about 1 mm, and an average grain diameter of preferably less than about 0.1 mm. In some embodiments, the average grain length may be at least about 10 mm. The average grain diameter is at least about 5 mm. The metal may include one or more grains having an aspect ratio of grain length to diameter of at least 10:1, preferably 100:1 or more.

To achieve such a controlled microstructure, the implant or implant sub-component may processed from a melt by a process that controls the direction of solidification along its elongated axis. This may be achieved through controlled heat removal (under-cooling) at one end of the elongated structure so that crystal nucleation and propagation is driven down its length (z axis in FIG. 2), while crystal formation in the directions perpendicular to elongated axis are retarded by keeping those surfaces at an elevated temperature with insufficient under-cooling for nucleation. Additional mechanical forming processes can be practiced following directional solidification to achieve the final implant geometry, if the thermal treatments do not result in a re-crystallization that reverts the structure to polycrystalline.

A suitable process for forming at least a portion of an implant from a melt is the Ohno process. The Ohno process, typically used to form copper wires, is described in the literature. See, e.g.:
1. A. Ohno Casting of Near Net Shape Products, Edited by Y. Bahai, The Metallurgical Society (1988) 177;
2. X. Fan, Y. Cai Y, P. Wei, J. Li and H. Fu, Continuous casting technology of single crystal metals, Chinese Journal of Materials Research (June 1996) Vol. 10, No. 3, pp. 264-266;
3. Z. M. Zhang, T. Lu, C. J. Xu and X. F. Guo, Microstructure of binary Mg—Al eutectic alloy wires produced by the Ohno continuous casting process, ACTA Metall. Sin. (Engl. Lett.) Vol. 21, No. 4 (August 2008) pp. 275-281;
4. M. H. Kim, H. H. Jo and H. Y. Cho, Operating parameters for the continuous unidirectional solidification of the Al-1 wt. % Si Alloy drawn to fine wire, Metals and Materials, Vol. 6, No. 6 (2000) pp. 491-495; and
5. Y. J. Kim and S. Kou, An Experimental Study on Process Variables in Crystal Growth by Ohno Continuous Casting, Metallurgical Transactions A, Volume 19A (July 1988) pp. 1849. Each of these references is incorporated by reference herein in its entirety.

In particular, the Ohno process is a continuous casting process that uses a heated mold, rather than a cooled mold. The mold is heated slightly above the melting point of the metal to be solidified. This has the result that no new grains can nucleate at the mold wall. Solidification is restricted to the contact area between the melt and the dummy rod or single crystal seed, which is withdrawn from the melt. The mold can be positioned vertically upward, vertically downward, or horizontal. The melt stays in the mold even when the mold is not positioned vertically upward, as the die diameter is small, and grips or pinch rollers are needed to pull the wire out of the mold.

An advantage of the Ohno process is that it can be used for directional solidification or crystal growth, and ingots or crystals of unlimited length may be produced. The resulting material has a smooth surface and inner quality due to the fact that impurities are moved to the boundaries, resulting in a pure crystal. In addition superior mechanical properties are achieved due to the resulting directionally solidified microstructure.

One way to create a wire using the Ohno process is to utilize a crucible furnace with a melt level control, a heated mold with a small diameter channel, a cooling device to cool the wire after it exits the mold, and pinch rolls to pull the wire away from the mold.

Wire/bar drawing, a metalworking process known to those of skill in the art, allows for successive reductions in diameter of the bar/wire by pulling the wire/bar through successively smaller diameter dies. The successive reductions in diameter result in expansion of the length of the wire. The die is typically mounted on a draw bench and the end of the wire is placed in grips so that the rest of the wire may be pulled through the die. The process of drawing improves the mechanical properties of the wire due to work hardening.

In an exemplary process, eutectic Mg—Al wires of 5 mm in diameter with mirror-smooth surface may be continuously solidified with a casting speed 10 mm/min, a mold exit temperature of 450° C., a static pressure head of the melt of 5 mm, a flow rate of cooling water 30 L/h, and a mold-cooling water distance 20 mm. Under these casting conditions, the wires solidify just outside of the mold exit.

Various metals may be suitable for embodiments of the invention, including metallic alloys of magnesium, iron, zinc, calcium, manganese and/or combinations thereof. In particular, an elongated metallic element may include more than about 50% by weight a metal, such as magnesium, iron, zinc, calcium, and/or manganese metals and/or combinations or alloys thereof, and is preferably substantially free of rare earth metals. Substantially free of rare earth metals, as used herein, means that less than 0.1% (by weight) of the metallic alloys includes rare earth metals. Anything less than 0.1% is in the hundreds parts per million range, which is below the FDA threshold in safety profiles of individual impurities in drugs. At that level, rare earth metals also do not have a significant effect on corrosion properties. Rare earth and other high atomic number metals and their compounds are undesirable in implants because they are largely insoluble in physiologic fluids, which significantly delays absorption by local tissue.

In some embodiments, the metallic alloy may be at least 80% Mg, with the balance including one or more of the elements Ca, Mn, Zn, Fe, plus trace elements. It may be preferable to use pure Mg as a basis for the alloy, with no inclusion of rare earth metals.

Figure 3:
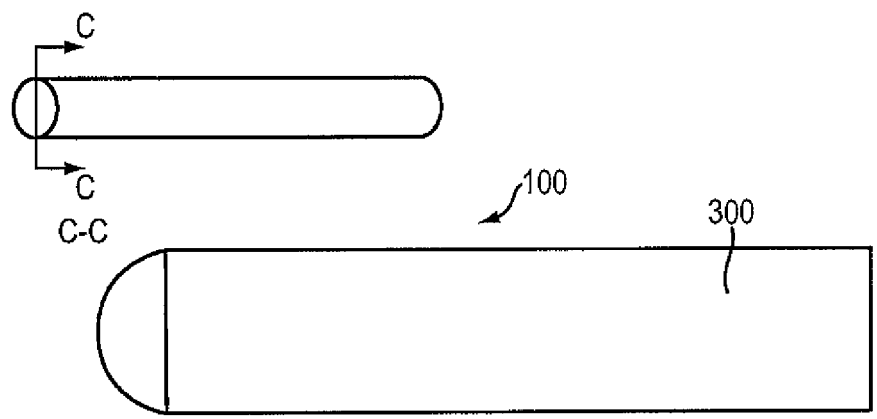
FIG. 3 is a schematic diagram of an elongated implant or sub-component formed of a single crystal that is essentially without grain boundaries in accordance with an embodiment of the invention.

Referring to FIG. 3, in some embodiments, a segment of an elongated implant or sub-component processed by directional solidification yields a single columnar crystal 300 that extends essentially the full functional length of the implant.

The elongated metallic element may define at least a portion of the bioabsorbable implant. The elongated metallic element may include a wire. The wire may have a diameter of less than about 02 mm. For intraluminal devices like stents, diameters above about 0.2 mm may create too much trauma to the vessel wall. On the other hand, in some embodiments such as ligating clips or suture anchors, diameters up to several mm may be preferred.

As discussed below, the elongated metallic element may include a wire formed into at least one discrete bioabsorbable expandable metal ring, or a wire formed into a bioabsorbable continuous helical sinusoid. The metal ring may be formed from welded wire forms or by laser micro-machining of metal tubing.

Figure 4:
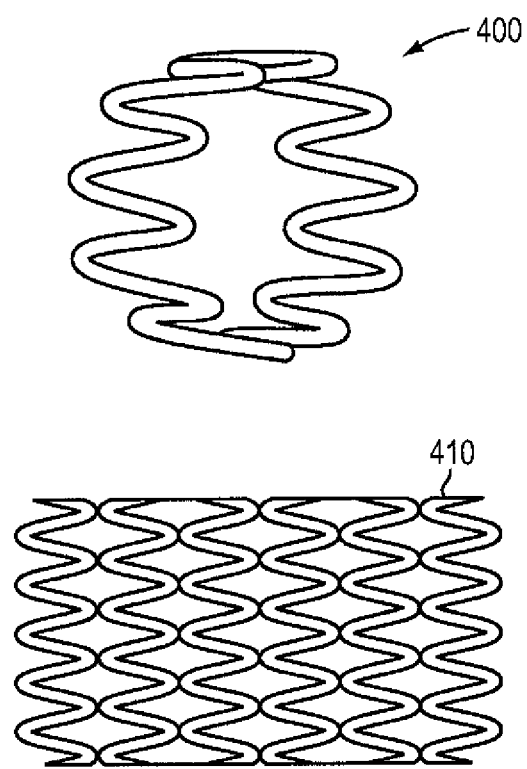
FIG. 4 is a schematic diagram of a segment of directionally solidified alloy formed into a sub-component of an implant, in accordance with an embodiment of the invention.

The bioabsorbable implant may be any one of various devices, such as an intraluminal device. Referring to FIG. 4, a segment of directionally solidified alloy may be formed into a sub-component of an implant, i.e., a ring element 400 of a balloon expandable coronary stent 410.

Figure 5:
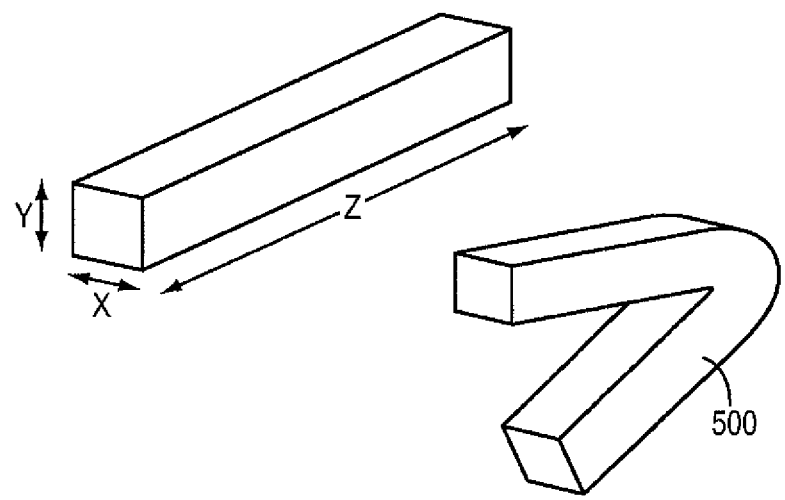
FIG. 5 is a schematic diagram of a segment of directionally solidified alloy formed into a ligating clip, in accordance with an embodiment of the invention.
Figure 5:
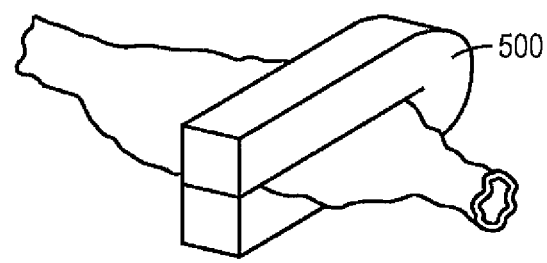

The bioabsorbable implant may also be a ligating clip or a ligating clip component. In particular, referring to FIG. 5, a segment of directionally solidified alloy may be formed into a ligating clip 500 for tubular anatomical structures.

Figure 6:
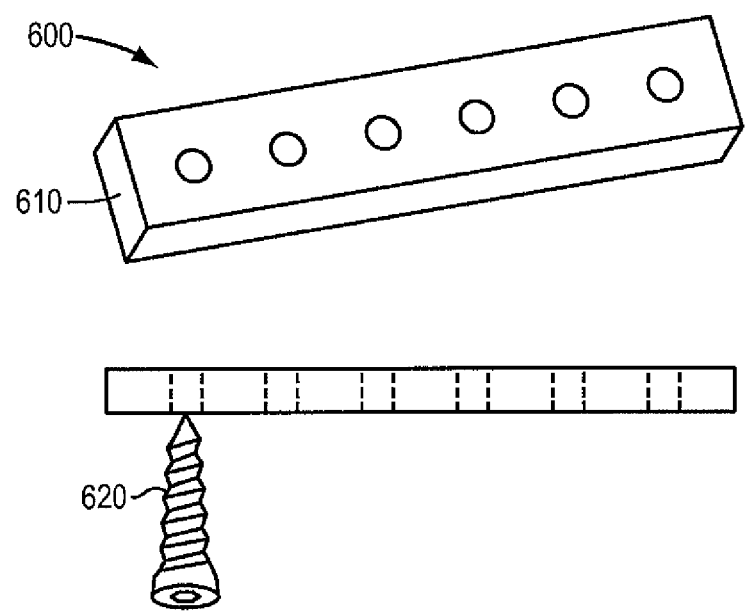
FIG. 6 is a schematic diagram of directionally solidified alloy formed into a bone fixation device, in accordance with an embodiment of the invention.

Referring to FIG. 6, in some embodiments, the bioabsorbable implant is a bone fixation device 600 for fracture fixation, e.g., a plate 610, a pin, or a screw 620.

Figure 7:
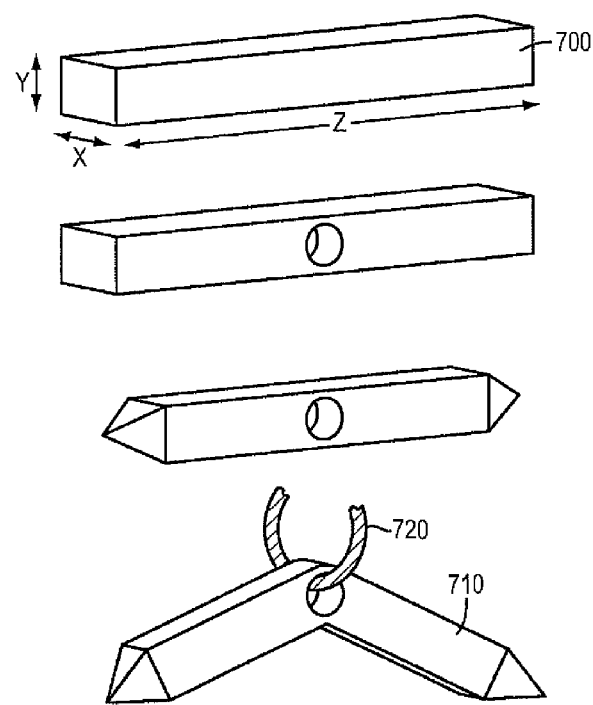
FIG. 7 is a schematic diagram of a segment of directionally solidified alloy blank formed into a bone anchor, in accordance with an embodiment of the invention.

In other embodiments, the bioabsorbable implant is a bone-to-soft-tissue fixation device, e.g., a suture anchor, an interference screw, or a cross pin. For example, referring to FIG. 7, a segment of directionally solidified formed alloy, produced as discussed above, in the form of a blank 700 may be formed into a bone anchor 710 (also referred to as a suture anchor) for soft tissue reattachment by means of a suture 720.

Several key features of the directionally solidified structures differentiate their performance from polycrystalline alloys of the same alloy composition and geometry (cross-sectional area). First, they retain strength and physical integrity longer under corrosion conditions (in vivo) due to the elimination of vulnerable grain boundaries that contain Fe and other impurities that result in mini-galvanic cells with the Mg. For many implant applications, maintaining strength and integrity through the early healing periods is critical for both soft and hard tissue applications.

Secondly, they inherently possess better ductility and fatigue resistance, since mechanical failure (in the absence of corrosion) is most often initiated at a micro-crack that forms at the interface of two grains under tensile or compressive load. This feature of directionally solidified alloys is currently utilized for critical load bearing non-implant applications such as turbine rotors.

Thirdly, because the loss of strength and mass is through surface corrosion and erosion, they degrade more "gracefully" in vivo, i.e. fragmentation starts later and with smaller and less injurious intermediate fragments.

Figure 8A:
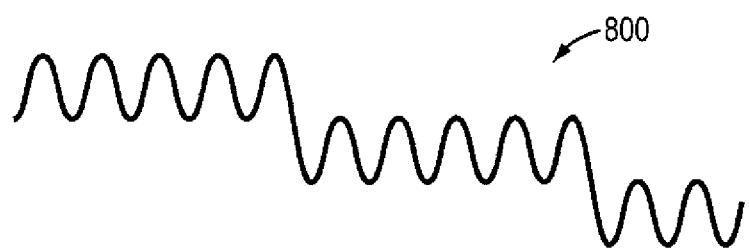
FIG. 8a is a schematic diagram of a wire formed into a continuous sinusoidal-like wave form in accordance with an embodiment of the invention.
Figure 8B:
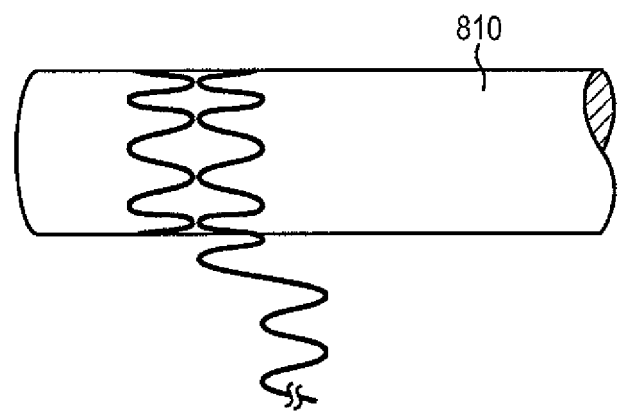
FIG. 8b is a schematic diagram illustrating the continuous sinusoidal-like wave form of FIG. 8a being wrapped around a mandrel, in accordance with an embodiment of the invention.
Figure 8C:
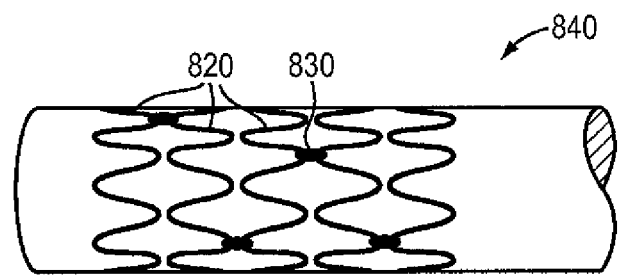
FIG. 8c is a schematic diagram of a bioabsorbable continuous helical sinusoid, in accordance with an embodiment of the invention.

A preferred embodiment of a bioabsorbable implant is a bioabsorbable helical continuous sinusoid. This structure may include a wire formed into the sinusoid; the wire may define either a continuous single grain or a columnar microstructure. Referring to FIGS. 8a and 8b, a helical continuous sinusoid may be defined as a wire-form tubular structure made from a wire that is first formed into a continuous sinusoidal-like wave form 800, and that is secondly wrapped in a helical configuration around a cylindrical mandrel 810 to form a tubular but mechanically unstable structure. Referring to FIG. 8c, thirdly, the adjacent rows of ring-like structures 820 of the wire wave form 800 are connected at discrete contact points 830 to provide mechanical integrity, either by longitudinal absorbable polymer connectors, or by known metal welding techniques to define a helical continuous sinusoid 840.

A pharmaceutically active agent may be disposed over at least a portion of the helical continuous sinusoid 840. The pharmaceutically active agent may be one of many suitable materials. For example, it may be a potent anti-proliferative to human smooth muscle cells, and a chemoactive agent suitable for cancer treatment. The agent may be a taxane, such as Paclitaxel, its derivatives and prodrugs thereof. In some embodiments, the agent may be a known mTOR agent such as sirolimus or everolimus, their derivatives and prodrugs thereof. The implant may locally deliver both a taxane and a mTOR agent. The active agent may be eluted at a controlled rate through formulation with a biodegradable polymer.

One key aspect of one design in accordance with an embodiment of the invention is a more controlled, graceful degradation process than that of existing fully absorbable metal stent designs. In previous attempts to form absorbable metal stents, the integral metal longitudinal connecting elements degraded at a similar rate to the structural ring elements. At intermediate fragmentation stages, long and wide stent fragments may be formed consisting of multiple ring fragments and intact metal connectors. The shape and size of these fragments make them problematic relative to obstructing the vessel lumen. In one embodiment, the fragment size is reduced by using longitudinal connectors comprised of an absorbable polymer with significantly faster degradation kinetics than the metal rings. In another embodiment, the high surface area and favorable surface chemistry of the polymeric longitudinal connectors contribute to rapid tissue coverage and integration of the implant into the vessel wall.

Figure 9:
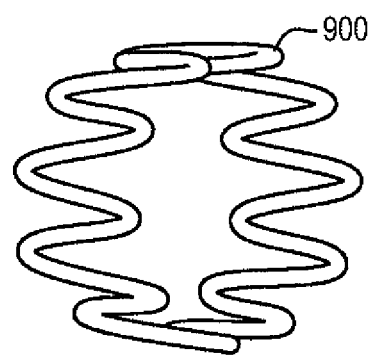
FIG. 9 is a schematic diagram of a single expandable ring made of an absorbable magnesium alloy wire that has been mechanically formed and welded in accordance with an embodiment of the invention.

Referring to FIG. 9, a single discrete bioabsorbable expandable metal ring 900 may be made from a wire of an absorbable magnesium alloy wire that has been mechanically formed and welded. The ring 900 may also be formed from any of the other alloys discussed above, including iron, zinc, calcium, and/or manganese metals or alloys, or any other material suitable for forming a bioabsorbable implant.

Figure 10:
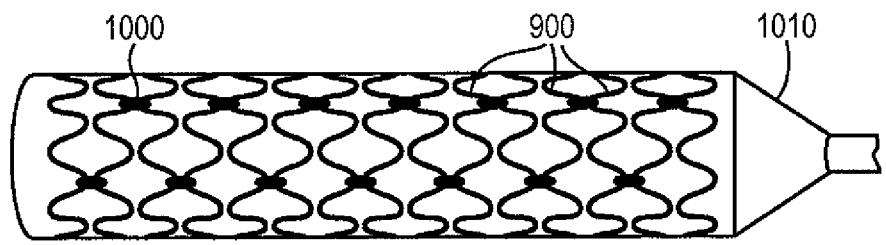
FIG. 10 is a schematic diagram of a plurality of expandable metal rings connected by discrete loops of absorbable polymer in accordance with an embodiment of the invention.

Referring to FIG. 10, a plurality of expandable metal rings 900 formed from wire may be connected by discrete loops of absorbable polymer, i.e., flexible longitudinal connector 1000, and mounted on a balloon catheter 1010. The plurality of rings may include a first discrete bioabsorbable expandable metal ring and a second discrete bioabsorbable expandable metal ring, with at least one flexible longitudinal connector, including an absorbable polymer, connecting the first and second discrete expandable metal rings. A coating including a pharmaceutically active agent may be disposed over at least a portion of at least one of the first and second metal rings and the longitudinal connector. At least one of the expandable metal rings may include a wire defining a single grain or a columnar microstructure.

One or more of the flexible longitudinal connectors may include a biodegradable homopolymer of an aliphatic polyester, such as lactic acid, lactide, glycolic acid, glycolide, caprolactone, dioxanone, trimethylcarbonate, and co-polymers and Mends thereof.

The pharmaceutically active agent may be one of many suitable materials. For example, it may be a potent anti-proliferative to human smooth muscle cells, and a chemoactive agent suitable for cancer treatment. The agent may be a taxane, such as Paclitaxel, its derivatives and prodrugs thereof. In some embodiments, the agent may be a known mTOR agent such as sirolimus or everolimus, their derivatives and prodrugs thereof. The implant may locally deliver both a taxane and a mTOR agent. The active agent may be eluted at a controlled rate through formulation with a biodegradable polymer.

Figure 11:
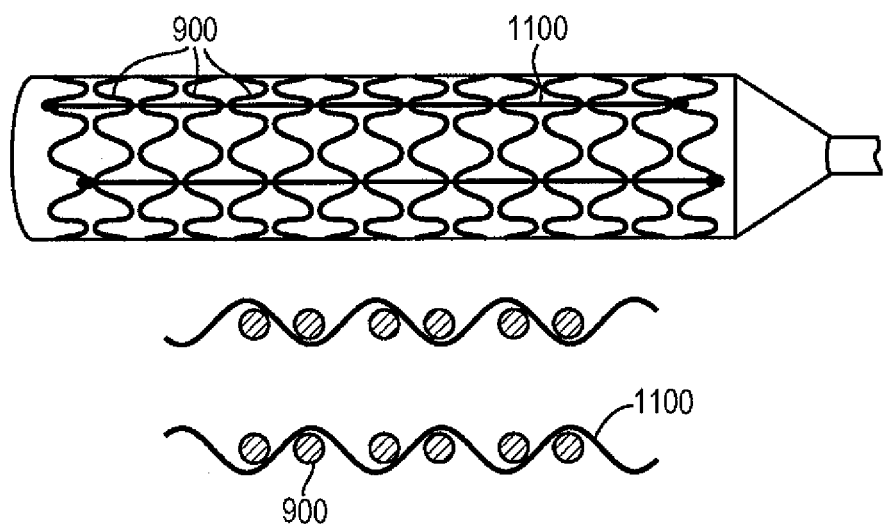
FIG. 11 is a schematic diagram of a plurality of expandable metal rings connected longitudinally by interwoven filaments made of absorbable polymer, with connectors extending continuously the full length of the implant in accordance with an embodiment of the invention.

Referring to FIG. 11, a plurality of expandable metal rings 900 or a helical continuous sinusoid may be connected longitudinally by interwoven filaments 1100 made of absorbable polymer. A longitudinal cross-sectional view shows the metallic rings 900 and interwoven filaments 1100. The helical continuous sinusoid 840 may also be similarly connected longitudinally by interwoven filaments 1100 (not shown).

At least one of the flexible longitudinal connectors may include directionally oriented absorbable filaments extending along a length of the bioabsorbable implant.

Figure 12A:
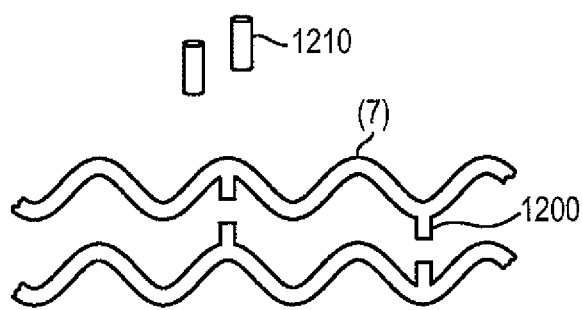
FIG. 12a is a schematic diagram of segments of expandable metal rings with stud features and a small diameter extruded tube of flexible absorbable polymer cut to length in accordance with an embodiment of the invention.
Figure 12B:
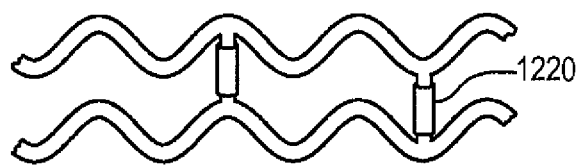
FIG. 12b is a schematic diagram of an assembled composite implant with the tube connecting the stud features on adjacent segments in accordance with an embodiment of the invention.

Referring to FIGS. 12a and 12b, at least one of the expandable metal rings 900 may define a stud feature 1200. The stud is configured to allow for mechanical connection of adjacent ring segments. A hollow, small diameter extruded tube of, e.g., flexible absorbable polymer of PLGA may be cut to length 1210 and interference fit over the opposing stud features 1200 to form a longitudinal connector 1220.

Figure 13:
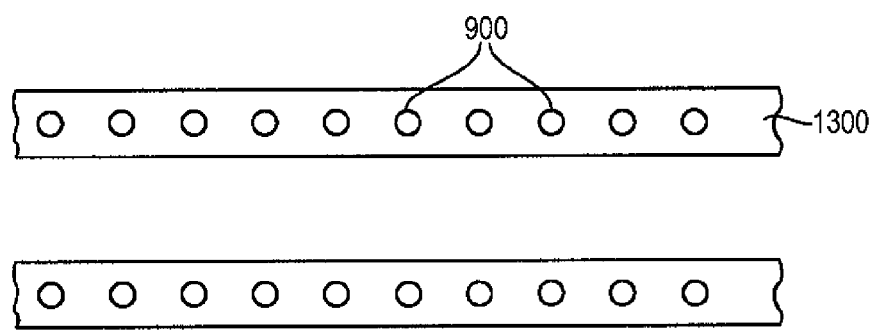
FIG. 13 is a longitudinal cross sectional view of a plurality of expandable metal rings connected by injection-molded longitudinal connectors of flexible absorbable polymer in accordance with an embodiment of the invention.

Referring to FIG. 13, a plurality of expandable metal rings 900 or a helical continuous sinusoid 840 may be connected by injection-molded longitudinal connectors 1300 of flexible absorbable polymer. Accordingly, in some embodiments, the flexible longitudinal connectors may include extruded tubes of absorbable polymer.

Figure 14:
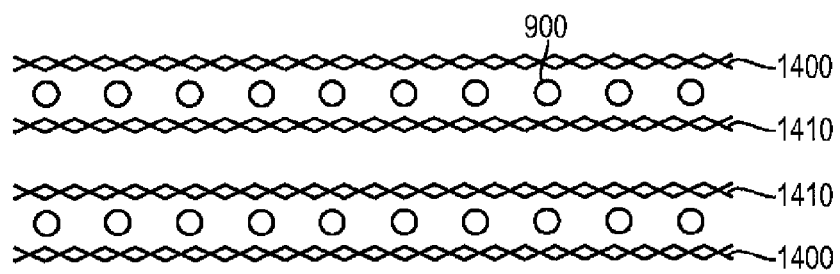
FIG. 14 is a longitudinal cross-sectional view of a 3-layer sandwich construction of braided absorbable polymer filaments on outer and inner layers, encapsulating a middle layer of expandable metal rings in accordance with an embodiment of the invention.

Referring to FIG. 14, a 3-layer sandwich construction may include braided absorbable polymer filaments on outer 1400 and inner layers 1410, encapsulating a middle layer of expandable metal rings 900.

In some embodiments, at least one of the expandable rings form an eyelet adapted for coupling with the at least one flexible longitudinal connector (see eyelet 5 in FIG. 14).

Figure 15:
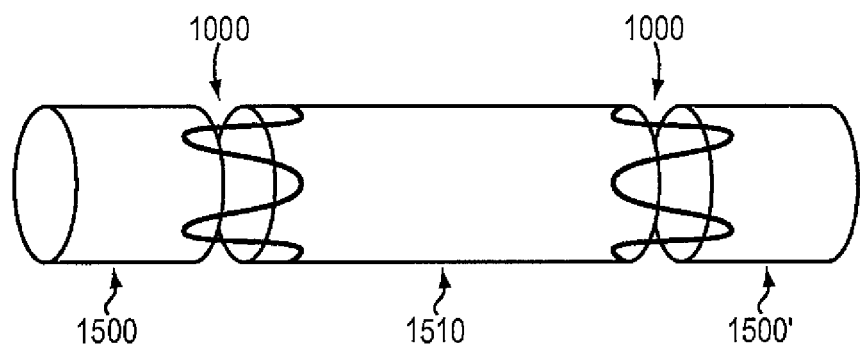
FIG. 15 is a schematic diagram of a hybrid stent including thin ring segments made from a biostable and radio-opaque material, a larger center ring segment made from an absorbable magnesium alloy, and filament connectors between segments made of absorbable polymer in accordance with an embodiment of the invention.

Referring to FIG. 15, a hybrid stent may include thin proximal and distal ring segments 1500, 1500' made from a biostable and radio-opaque material, a larger center ring segment 1510 including, e.g., a plurality of rings 900 made of a bioabsorbable magnesium alloy (or any or the other bioabsorbable alloys discussed herein) or a helical continuous sinusoid 840, and filament connectors, e.g., longitudinal connectors 1000 made of a bioabsorbable polymer such as PLGA. As seen in the figure, the bioabsorbable expandable metal ring 900 may be disposed adjacent at least one of the biostable rings 1500, 1500', and at least one flexible longitudinal connector 1000 is disposed between at least two adjacent rings. A coating including at least one pharmaceutically active agent may be disposed over at least a portion of one ring.

At least one of the biostable rings may be a laser-machined hypo-tube including cobalt, chrome, stainless steel, titanium, and/or iron.

At least one of the flexible longitudinal connectors may include a biodegradable homopolymer and/or an aliphatic polyester such as lactic acid, lactide, glycolic acid, glycolide, caprolactone, dioxanone, trimethylcarbonate, and/or co-polymers and blends thereof.

At least one of the flexible longitudinal connectors may include directionally oriented absorbable filaments extending along a length of the bioabsorbable implant and/or extruded tubes of absorbable polymer such as PLGA.

As in other embodiments described herein, the pharmaceutically active agent may be one of many suitable materials. For example, it may be a potent anti-proliferative to human smooth muscle cells, and a chemoactive agent suitable for cancer treatment. The agent may be a taxane, such as Paclitaxel, its derivatives and prodrugs thereof. In some embodiments, the agent may be a known mTOR agent such as sirolimus or everolimus, their derivatives and prodrugs thereof. The implant may locally deliver both a taxane and a mTOR agent. The active agent may be eluted at a controlled rate through formulation with a biodegradable polymer.

Figure 16:
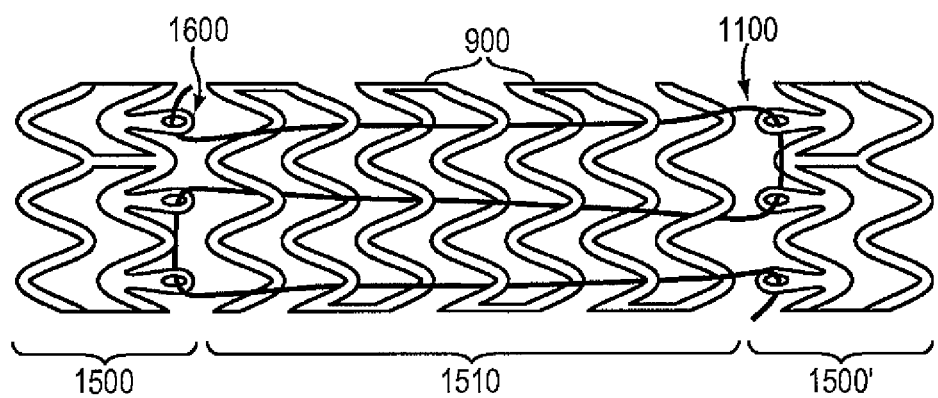
FIG. 16 is a schematic diagram of eyelet design features that facilitate the interlacing of ring segments by continuous filament connectors in accordance with an embodiment of the invention.

Referring to FIG. 16, at least one of the discrete biostable rings 1500, 1500' may define an eyelet 1600 and/or a stud configured to couple with at least one flexible longitudinal connector, e.g., interwoven filaments 1100. The eyelet design features 1600 facilitate the interlacing of the laser cut biostable proximal and distal ring segments 1500, 1500' by continuous filament connectors 1100 that transverse the center bioabsorbable segment 1510 including a plurality of bioabsorbable rings 900 or a helical continuous sinusoid 840.

Figure 17:
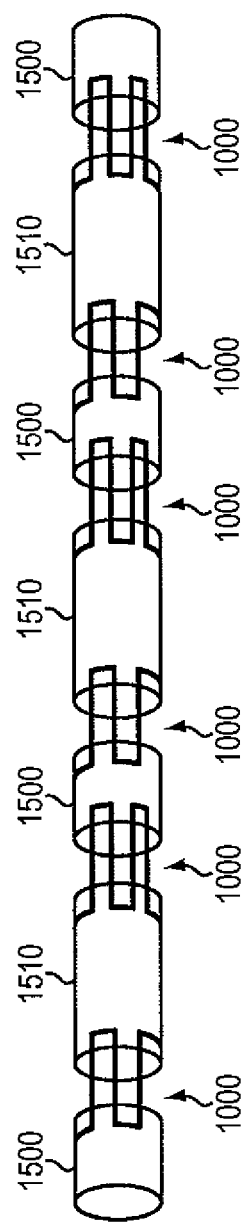
FIG. 17 is a schematic diagram of a hybrid stent with a plurality of alternating biostable and absorbable ring segments and absorbable polymer connectors in accordance with an embodiment of the invention.

Referring to FIG. 17, a hybrid stent may include a plurality of alternating biostable 1500 and bioabsorbable ring segments 1510 and bioabsorbable polymer connectors 1000.

Advantages and improvements of the processes, methods and devices of the present invention are demonstrated in the following examples. These examples are illustrative only and are not intended to limit or preclude other embodiments of the present invention.

Example 1

A 99.99% pure magnesium rod of 20 cm length and 5 mm diameter may be directionally solidified from the melt in an induction-heated graphite mold equipped with means for rapid cooling from a single end, e.g., the Easyheat 0112 system available from Ameritherm, based in Scottsville, N.Y. A center section of the rod may be mechanically reduced to a diameter of 1.5 mm, and the rod may then be drawn at an elevated temperature to a wire diameter of 125 microns. The wire may be cut to length, and bent on a wire forming machine into a sinusoidal geometry with a peak-to-valley height of 1.25 mm. A 6 crown ring may be formed by bending a cut length of the linear wire form around a circular mandrel, clamping it in place with opposing wire ends coming in direct contact and overlapped, followed by laser welding to form a lap joint. The metal stent rings may then be electro-polished to a final wire diameter of 120 microns while smoothing weld joints. A series of 12 rings may be welded together at 3 locations per ring to form a 15 mm long vascular stent. The stent platform may be spray coated with 200 microgram coating weight (dry) of D,L PLA-Paclitaxel with a 5% drug load, predominantly on the external or abluminal surface. The drug coated stent may be crimped on an angioplasty balloon catheter, and sterilized by e-beam sterilization.

Example 2

A metal including, e.g., 100% magnesium may be continuously cast by the Ohno continuous casting process used for preparing single crystal fine copper wire, and then drawn to a final diameter of 110 microns, with a length of several miles. The wire may be cut to length sufficient to define one discrete ring, and bent on a wire forming machine into a sinusoidal geometry with a peak to valley height of 1.0 mm. A 6 crown ring may be formed by bending a cut length of the linear wire form around a circular mandrel, clamping it in place with opposing wire ends coming in direct contact and overlapped, followed by laser welding to form a lap joint. The metal stent rings may then be electro-polished to a final wire diameter of 100 microns while smoothing weld joints. Then a stable and dense MgO layer of approximately 1 micron may be formed through electrochemical techniques to passivate the implant surface. A series of 15 rings may be interconnected with filaments of absorbable co-polymer of 10% lactide-90% glycolide to form a vascular stent. The stent platform may be spray coated with 200 microgram coating weight (dry) of D,L PLA-Paclitaxel with a 7.5% drug load. The drug coated stent may be crimped on an angioplasty balloon catheter, and sterilized by ethylene oxide sterilization.

Example 3

A ligating clip may be made from 1.5 mm×1.5 mm square stock a magnesium-based directionally solidified alloy. The square blank may be cast in a heated tool that is equipped for super cooling from one end, resulting in a microstructure of columnar grains extending for its entire length. The square blank may be cut to length, electro-polished, and then passivated with the formation of dense MgO layer. The blank may be formed into an open "V" clip by hot working to form the hinge point, and cold coining of the outer surfaces to form details for engagement and retention within the jaws of a clip applier. The cartridge of clips may be packaged and sterilized by conventional gamma sterilization at a minimum dose of 3.0 MRads. The clips may retain integrity for 4 weeks in vivo, and may be used for small vascular vessel ligation, or for reproductive sterilization.

Example 4

A bone fixation device may be made from a high purity alloy of 98% Mg-2% Ca that is directionally solidified into a 2.5 mm cylindrical blank, which is subsequently tapered in a secondary grinding process. The pin may then be electro-polished to remove surface contaminants and then treated by electrochemical means to form a dense magnesium oxide layer. The pin preferably possesses the necessary mechanical strength and ductility for an interference fit for insertion into a pre-drilled hole in two bone fragments. The pin preferably retains physical integrity and prevents micro-motion between the fragments for period of 12 weeks, and is subsequently fully absorbed.

Example 5

A directionally solidified wire of pure Mg with 10-90 PLGA filament longitudinal connectors and spray coated paclitaxel-PLA coating may be made as follows. High purity magnesium may be directionally solidified and drawn into a 125 micron diameter round wire. The wire may have an ultimate tensile strength of 125 MPa and elongation to break greater than 25%. The wire may be formed on a four slide wire forming machine into conventional sinusoidal or racetrack geometry with a ring height of 1.0 mm in the crimped state. A 6 crown ring may be formed by bending the linear wire form around a circular mandrel, clamping it place with opposing wire ends coming in direct contact and overlapped, followed by laser welding to form a lap joint. The metal stent rings may then electropolished to a final wire diameter of 120 microns while smoothing weld joints. Longitudinal connectors may be made from 10-90 PLGA, by taking 12 rings and lacing or weaving them together axially with 3 filament bundles, each equivalent to 5-0 Vicryl suture, and spaced at approximately 120 degrees apart around the ring circumference. The final composite assembly may be heat set at 60° C. to a final length of 15 mm. The assembly may be spray coated with 200 microgram coating weight (dry) of D,L PLA-Paclitaxel with a 5% drug load, predominantly on the external or abluminal surface. The drug-coated stent may be crimped on an angioplasty balloon catheter, and sterilized by e-beam sterilization.

Example 6

A magnesium alloy laser-cut ring with extruded tubular 5050 PLGA polymer longitudinal connectors and a coating of 8020 PLGA polymer with 10% paclitaxel may be made as follows: A magnesium alloy may be formed into a 2.0 mm (outside diameter) hypo-tube. The hypo-tube may be laser cut into ring segments, with 8 crowns per ring. Each ring segment may have at least 2 elongated stud features of 0.4 mm length and facing matching studs on an opposing ring. The rings may then be connected by flexible longitudinal connectors of 1.0 mm long tubular extrusions of 50-50 PLGA placed over each stud. Fourteen rings with 13 sets of connectors may be assembled into a 20 mm stent, expandable to 3.0 mm diameter. The assembly may be spray coated with a 250 microgram coating weight (dry) of 8020 PLGA polymer pre-compounded with 10% (by weight) Paclitaxel drug. The drug coated stent may be crimped on an angioplasty balloon catheter and sterilized by e-beam.

Example 7

Hyper-fine grain, Mg—Ca alloy wire with Polydioxanone polymer longitudinal connectors and a D,L-PLA-Sirolimus Drug Coating may be made as follows: High purity magnesium-1% Ca with grain size below 5 microns may be drawn and annealed into a 100 micron wire. The wire may be formed into a 6 crown design and welded into a ring. Twelve rings may be equally spaced in a cavity of a steel mold, and poyldioxanone (PDO) in a solvent solution may be vacuum injected into the cavity. Following secondary processes for solvent removal and annealing, the structure may be 15 mm long with 12 metal ring segments. The assembly may be spray coated with 200 microgram coating weight (dry) comprised of 50% D,L PLA and 50% Sirolimus.

Example 8

A Mg-alloy wire-PGA fiber braid with high load chemoactive agent was made as follows: An alloy of magnesium was melted and processed into 160 micron wire. The wire was formed into continuous sinusoid wave form and then wrapped in a helical geometry around a 4.0 mm cylindrical mandrel. The tubular helical structure rings were coupled by longitudinal polymer connectors of Vicryl 6-0 suture (available from Ethicon Inc. of Somerville N.J.). The finished tubular stent-like implant was 12 mm long and was coated with 120 micrograms (dry weight) of a 95% PLA-5% paclitaxel formulation with a manual pipette system. Following mounting on a balloon catheter and ethylene oxide sterilization, the device was used as a short term, luminal drug delivery platform for treatment of cancer of the esophagus.

Example 9

A 15 mm×3.5 mm diameter coronary stent may include 3 cylindrical or ring segments connected by longitudinal absorbable polymer element. The proximal and distal ring segment may be made from a 75 micron 316L stainless steel alloy wire that is formed into a sinusoidal waveform that is wrapped around a mandrel and welded to form a segment of 2.5 mm in length. The central ring segment may be formed from a Mg high purity alloy that is cast and drawn into a wire of 100 microns in diameter. The Mg wire may be formed on a multi-slide machine into a continuous sinusoidal waveform, wound on a mandrel, and laser welded at select connection points between subsequent rows of rings to form a segment of 8.0 mm in length. The three segments may be connected by interlacings of a 6-0 Vicryl absorbable PLGA suture, with an effective connector length of 0.5 mm each. The total length may equal 2.5+0.5+9+0.5+2.5=15 mm. The entire assembly may be coated with a formulation of approximately 6% Paclitaxel in 90-10 PLGA, crimped on an angioplasty catheter, packaged, and sterilized.

Example 10

A 20 mm×3.5 mm diameter coronary stent may include 3 cylindrical or ring segments connected by longitudinal absorbable polymer elements. The proximal and distal ring segments may be made by laser cutting a cobalt chrome hypo tube into an open cell stent geometry followed by electro-polishing down to an 80 micron strut thickness. The effective length when expanded may be 4 mm, and the design may include eyelet features to facilitate interlacing with adjacent segments. The central segment may be made of mono-crystalline magnesium wire that is formed into a continuous sinusoidal waveform that is wrapped on a cylindrical mandrel and laser welded at given intervals to form a flexible segment 12 mm in length. The proximal, central and distal rings may be connected in a similar manner by interlacing with 6-0 PDO absorbable monofilament sutures to form an intraluminal implant of about 20 mm in length. The entire assembly may be coated with a 50-50 formulation of Sirolimus and DL-PLA with approximately 10 micrograms drug per stent mm in length. The stent assembly may be crimped on an angioplasty balloon catheter, packaged and sterilized.

Example 11

A 30 mm×3.0 mm balloon expandable stent may be produced by means similar to the examples described as Example 10, with the exception of a third biostable segment at the center of the assembly. The stent may possess a proximal cobalt chrome laser cut segment of 4 mm, a magnesium wire form segment of 10 mm, a center cobalt chrome segment of 2 mm, another 10 mm magnesium segment, and the distal cobalt chrome ring segment of 4 mm, all interlaced together with 6-0 PDS absorbable monofilament suture. The entire assembly may be coated with a formulation of approximately 6% PT' x in 90-10 PLGA, crimped on an angioplasty catheter, packaged, and sterilized.

Those skilled in the art will readily appreciate that all parameters listed herein are meant to be exemplary and actual parameters depend upon the specific application for which the methods and materials of the present invention are used. It is, therefore, to be understood that the foregoing embodiments are presented by way of example only and that, within the scope of the appended claims and equivalents thereto, the invention may be practiced otherwise than as specifically described. Various materials, geometries, sizes, and interrelationships of elements may be practiced in various combinations and permutations, and all such variants and equivalents are to be considered part of the invention.

What is claimed is:

1. A bioabsorbable implant comprising:
a directionally solidified and elongated metallic element comprising more than 50% by weight a metal and being substantially free of rare earth elements, the elongated metallic element defining at least a portion of the bioabsorbable implant and comprising a wire formed into a discrete bioabsorbable expandable metal ring, the metal defining at least one of (i) a continuous single grain having an aspect ratio of grain length to grain diameter of at least 10:1 and (ii) a columnar microstructure including one or more columnar grains extending substantially the entire length of the implant, the one or more columnar grains each having an average grain length of at least about 1 mm and an average grain diameter of less than about 3 mm;
at least two biostable ring elements, each biostable ring element comprising a biostable and radio-opaque metallic alloy, the bioabsorbable expandable metal ring being disposed adjacent to at least one of the biostable ring elements;
at least one flexible longitudinal connector comprising a bioabsorbable polymer, the connector being disposed between at least two adjacent rings; and
a coating comprising at least one pharmaceutically active agent disposed over at least a portion of one ring;
wherein the metal is configured to exhibit enhanced strength and physical integrity post-implantation by being substantially free of grain boundaries containing impurities.

2. The bioabsorbable implant of claim 1, wherein the metal is selected from the group consisting of magnesium, iron, zinc, calcium, manganese, and combinations thereof.

3. The bioabsorbable implant of claim 1, wherein at least two of the biostable ring elements comprise a laser-machined hypo-tube comprising at least one of cobalt, chrome, stainless steel, titanium, and iron.

4. The bioabsorbable implant of claim 1, wherein at least one of the biostable ring elements defines at least one of an aperture and a stud configured to couple with the at least one flexible longitudinal connector.

5. The bioabsorbable implant of claim 1, wherein the at least one flexible longitudinal connector comprises at least one of a biodegradable homopolymer and an aliphatic polyester selected from the group consisting of lactic acid, lactide, glycolic acid, glycolide, caprolactone, dioxanone, trimethylcarbonate, and co-polymers and blends thereof.

6. The bioabsorbable implant of claim 1, wherein the at least one flexible longitudinal connector comprises at least one of directionally oriented absorbable filaments extending along a length of the bioabsorbable implant and extruded tubes of absorbable polymer.

7. The bioabsorbable implant of claim 1, wherein the pharmaceutically active agent is selected from the group consisting of a potent anti-proliferative to human smooth muscle cells, taxane, an mTOR agent, and a chemoactive agent suitable for cancer treatment.

8. The bioabsorbable implant of claim 1, wherein the elongated metallic element defines at least a portion of the bioabsorbable implant and comprises more than about 80% by weight of the metal.

9. The bioabsorbable implant of claim 8, wherein the metal is selected from the group consisting of magnesium, iron, zinc, and manganese, and combinations thereof.

10. The bioabsorbable implant of claim 9, wherein the one or more columnar grains each have an average grain diameter of less than about 0.2 mm.

11. The bioabsorbable implant of claim 1, wherein the wire has a diameter of less than about 0.2 mm.

12. The bioabsorbable implant of claim 1, wherein the elongated metallic element comprises <0.1 weight percent of rare earth metals.

13. A bioabsorbable implant comprising:
a directionally solidified and elongated metallic element substantially free of rare earth metals and comprising more than 50% by weight a metal selected from the group consisting of magnesium, iron, zinc, manganese and combinations thereof, the elongated metallic element defining at least a portion of the bioabsorbable implant and comprising a wire formed into a first bioabsorbable expandable metal ring and a second bioabsorbable expandable metal ring, the metal defining at least one of a continuous single grain and a columnar microstructure including one or more columnar grains extending substantially the entire length of the implant, the wire exhibiting enhanced strength and physical integrity post-implantation by being substantially free of grain boundaries containing impurities.

14. A bioabsorbable implant of claim 13, further comprising:
at least one flexible longitudinal connector comprising an absorbable polymer, the at least one flexible longitudinal connector being configured to connect the first and second expandable metal rings; and
a coating comprising a pharmaceutically active agent disposed over at least a portion of at least one of the first and second metal rings and the longitudinal connector.

15. The bioabsorbable implant of claim 14, wherein at least one of the expandable metal rings comprises a stud configured for coupling with an adjacent feature.

16. The bioabsorbable implant of claim 14, wherein at least one of the expandable rings forms an aperture adapted for coupling with the at least one flexible longitudinal connector.

17. The bioabsorbable implant of claim 14, wherein at least one flexible longitudinal connector comprises at least one of a biodegradable homopolymer and an aliphatic polyester selected from the group consisting of lactic acid, lactide, glycolic acid, glycolide, caprolactone, dioxanone, trimethylcarbonate, and co-polymers and blends thereof.

18. The bioabsorbable implant of claim 14, wherein the at least one flexible longitudinal connector comprises at least one of directionally oriented absorbable filaments extending along a length of the bioabsorbable implant and extruded tubes of absorbable polymer.

19. The bioabsorbable implant of claim 14, wherein the pharmaceutically active agent is selected from the group consisting of a potent anti-proliferative to human smooth muscle cells, taxane, an mTOR agent, and a chemoactive agent suitable for cancer treatment.

20. The bioabsorbable implant of claim 13, wherein the continuous single grain has an aspect ratio of grain length to grain diameter of at least 10:1 and the one or more columnar grains each have an aspect ratio of grain length to grain diameter of at least 10:1.

* * * * *

UNITED STATES PATENT AND TRADEMARK OFFICE
CERTIFICATE OF CORRECTION

PATENT NO. : 9,849,008 B2
APPLICATION NO. : 14/527937
DATED : December 26, 2017
INVENTOR(S) : Steckel et al.

It is certified that error appears in the above-identified patent and that said Letters Patent is hereby corrected as shown below:

In the Specification

Column 12, Line 53 - "Mends" should be --blends--.

Signed and Sealed this
Twenty-fifth Day of September, 2018

Andrei Iancu
*Director of the United States Patent and Trademark Office*